United States Patent [19]

Makowski et al.

[11] Patent Number: 5,284,588
[45] Date of Patent: Feb. 8, 1994

[54] METHOD AND SYSTEM FOR ALLOWING INCREASED MIGRATION ACROSS A LIPID BILAYER

[75] Inventors: Lee C. Makowski, West Newton; Hoshang F. Batliwala, Boston, both of Mass.

[73] Assignees: Trustees of Boston University, Boston, Mass.; General Electric Company, Schenectady, N.Y.

[21] Appl. No.: 818,240

[22] Filed: Jan. 8, 1992

[51] Int. Cl.⁵ .............................................. B01D 61/38
[52] U.S. Cl. .................................... 210/638; 210/649; 264/4.1; 264/4.3
[58] Field of Search .................... 210/679, 649, 638; 435/2; 436/520; 514/786; 424/45, 450, 94.2; 264/4.3, 4.1, 4.6

[56] References Cited

U.S. PATENT DOCUMENTS 4,766,229 8/1988 Kobayashi et al. .................. 55/68 X

OTHER PUBLICATIONS

Huestis et al., *J. Biol. Chem.* 261(34): 16274–16278 (1986).
Deckmann et al., *Biochemica et Biophysica Acta,* 821:334–340 (1985).
Bouma et al., *J. Biol. Chem.,* 252(19): 6759–6763.
Rand et al., *Biochem.,* 29:76–87 (1990).
Ostro et al., *Am. J. Hosp. Pharm.,* 46: 1576–1587 (1989).
Gruner, *J. Phys. Chem.,* 1989(93):7562–7570 (1989).

*Primary Examiner*—Frank Spear
*Attorney, Agent, or Firm*—Hamilton, Brook, Smith & Reynolds

[57] ABSTRACT

A method and system are disclosed for allowing significantly increased migration of a molecule across a lipid bilayer membrane. The method includes combining an aqueous solvent medium, in which the lipid bilayer membrane and the molecule are disposed, with a solute. The aqueous solvent medium, the lipid bilayer membrane and the molecule are then exposed to a sufficient partial pressure of the solute to cause the solute to dissolve in the aqueous solvent medium, whereby a significant portion of the solute migrates to the hydrophobic fatty acyl portion of the lipid bilayer membrane. The solute thereby allows a significantly increased migration of the molecule across the lipid bilayer membrane.

26 Claims, 5 Drawing Sheets

METHOD AND SYSTEM FOR ALLOWING INCREASED MIGRATION ACROSS A LIPID BILAYER

BACKGROUND OF THE INVENTION

Manipulation of molecules relative to living cells, such as drug delivery into cells or isolation of cell components, including, for example, integral membrane proteins, has been limited by the nature of living cell membranes. The integrity of living cells is maintained by cell membranes which include a bilayer of phospholipids. Phospholipids are comprised of a hydrophilic lipid head group and one or more hydrophobic fatty acyl chains They are characterized as being amphipathic because they have both a hydrophilic component and a hydrophobic component. A cell membrane lipid bilayer includes substantially aligned hydrophobic fatty acyl chains of the phospholipids and two layers of the hydrophilic lipid heads which shield the fatty acyl chains from a medium in which the cell is disposed.

The amphipathic nature of phospholipids causes cell membranes to be substantially impermeable to ions and, with the exception of water, most polar molecules Migration of nutrients and waste products across cell membranes are generally mediated by specific transport mechanisms of integral membrane proteins. Integral membrane proteins typically span cell membranes and include hydrophobic side chains at one portion of the protein surface and hydrophilic side chains at another portion of the protein surface. However, delivery of water-soluble molecules, such as many drugs, into a cell through a cell membrane is limited because the hydrophobic fatty acyl layer between the two hydrophilic lipid head group layers substantially prevents migration of the molecule from an aqueous medium, in which the cell is disposed, across the cell membrane and into the cell.

Attempts to improve delivery of drugs and other molecules across cell membranes have included, for example, modification of the molecule, encapsulation of the molecule in vesicles which are tailored for uptake into specific types of cells and attachment to other molecules which are actively transported across cell membranes. However, most methods of delivery involve either adulteration of the composition to which the cell is exposed or limiting the effectiveness of the molecule, such as in the case of delivering a drug, by changing the structure of the molecule.

The amphipathic nature of lipid bilayers and integral proteins also causes manipulation of cell membranes and isolation of integral proteins to be difficult. For example, isolation of cell components, such as integral membrane proteins, often requires that the cell component be solubilized. Integral membrane proteins are typically isolated by exposing cells which include the proteins to a medium having a surfactant disposed therein. The surfactant is present in an amount sufficient to exceed a critical micelle concentration, or CMC, whereby micelles are formed. Simultaneously, the cell membranes typically dissolve and the integral membrane proteins of the cells become incorporated into the micelles of the surfactant as the micelles form, thereby solubilizing the integral membrane proteins. Hydrophobic portions of the surfactant molecules cluster around the hydrophobic portion of the integral membrane protein while the hydrophilic portions of the surfactant molecules are exposed to the surrounding aqueous medium.

However, the solubilized membrane proteins are contained in protein-detergent micelles of heterogeneous size and shape. These heterogeneous populations are difficult to crystallize, and separation of individual proteins is often compromised. Attempts to increase the resolution of proteins separated from cell membranes generally employs solvents, such as ionic detergents or alcohols, that denature proteins, thereby reducing the utility and yield of the proteins isolated.

Therefore, a need exists for a method of allowing significantly increased migration of a molecule across a lipid bilayer which overcomes or minimizes the above-mentioned problems.

SUMMARY OF THE INVENTION

The present invention relates to a method and system for allowing significantly increased migration of a molecule across a lipid bilayer membrane.

The method includes combining an aqueous solvent medium, in which the lipid bilayer membrane and a molecule, which can migrate across the lipid bilayer membrane, is disposed, with a solute which, at a sufficient partial pressure of the solute, dissolves in the aqueous solvent medium. A significant portion of the dissolved solute migrates to a hydrophobic fatty acyl portion of the lipid bilayer membrane. The solute also allows significantly increased migration of the molecule across the lipid bilayer membrane when a significant portion of the solute is dissolved in the aqueous solvent medium and when a significant portion of the solute is disposed in the hydrophobic fatty acyl portion of the lipid bilayer membrane. The aqueous solvent medium and the lipid bilayer membrane are then exposed to a sufficient partial pressure of the solute to cause the solute to dissolve in the aqueous solvent medium, whereby a significant portion of the solute migrates to the hydrophobic fatty acyl portion of the lipid bilayer membrane, thereby allowing significantly increased migration of a molecule across the lipid bilayer membrane.

The system includes means for combining an aqueous solvent medium, in which the lipid bilayer membrane and a molecule, which can migrate across the lipid bilayer membrane, is disposed, with a solute, at a sufficient partial pressure of the solute, dissolves in the aqueous solvent medium. A significant portion of the dissolved solute migrates to a hydrophobic fatty acyl portion of the lipid bilayer membrane. The solute also allows significantly increased migration of the molecule across the lipid bilayer membrane when a significant portion of the solute is dissolved in the aqueous solvent medium and when a significant portion of the solute is disposed in the hydrophobic fatty acyl portion of the lipid bilayer membrane. Suitable means then expose the aqueous solvent medium and the lipid bilayer membrane to a sufficient partial pressure of the solute to cause the solute to dissolve in the aqueous solvent medium, whereby a significant portion of the solute migrates to the hydrophobic fatty acyl portion of the lipid bilayer membrane, thereby allowing significantly increased migration of a molecule across the lipid bilayer membrane.

This invention has many advantages. For example, the efficacy of integral membrane protein solubilization is significantly increased. In one embodiment, the method lowers the CMC of surfactants and enables use of significantly smaller surfactant molecules for solubilization of membrane proteins, thereby decreasing the size and increasing the homogeneity of protein-surfactant micelles consequently formed. Also, separation, characterization and crystallization of integral membrane proteins isolated from cell membranes are significantly improved by forming significantly smaller and more homogeneous protein-surfactant micelles according to the method of the invention. Further, significantly reduced amounts of surfactant can be employed to solubilize membrane components for subsequent purification. In addition, denaturation of membrane components during solubilization and isolation can be significantly diminished. The solute employed by the method of the present invention also essentially completely dissipates during a depressurization step which follows migration of the molecule across the cell membrane.

The present invention can also be employed for delivery of drugs, proteins, genetic material, or other foreign matter, either into a cell membrane or into the cytoplasm of a cell. In one embodiment, a compound, such as a drug, can be disposed in a vesicle by the method of the present invention and then transferred from the vesicle to a living cell without disrupting the integrity of the cell. In another embodiment, a compound disposed within a bilayer of a vesicle, can be transferred to the cell, according to the method of the invention, whereby the compound disposed within the lipid bilayer becomes integrated within the cell membrane.

DETAILED DESCRIPTION OF THE INVENTION

Figure 1:
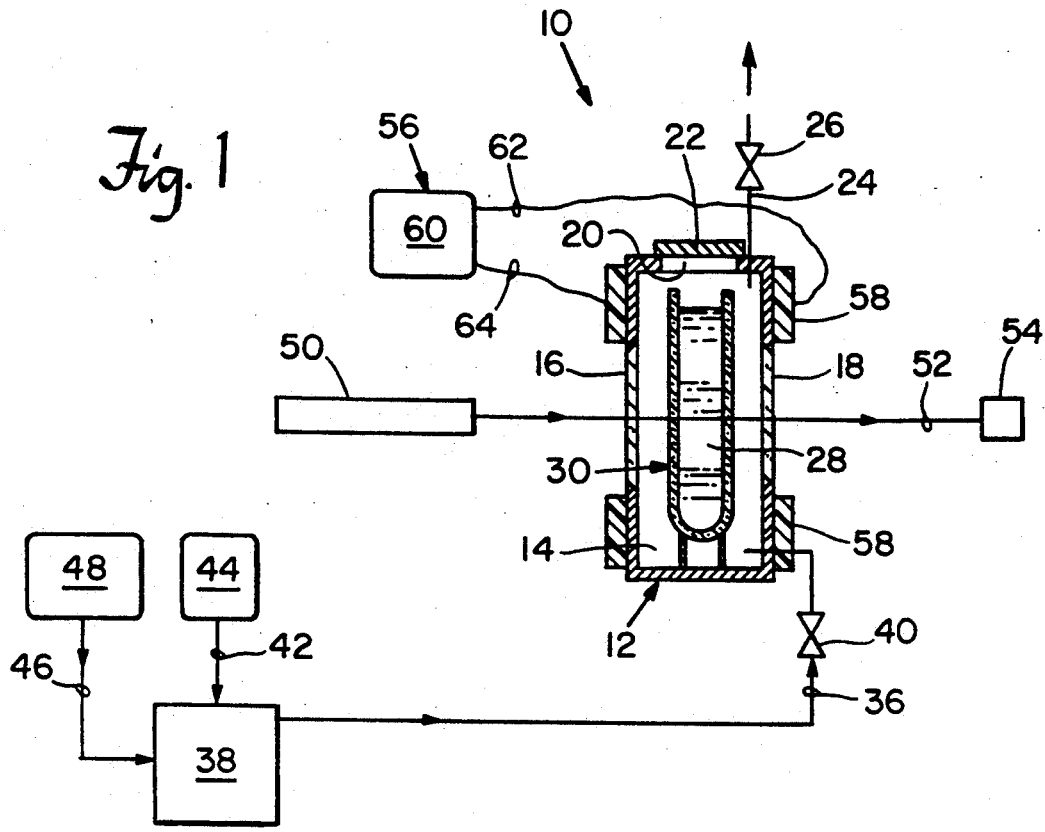
FIG. 1 is a schematic representation of one embodiment of a system for conducting the method of the invention.

The features and other details of the method of the invention will now be more particularly described with reference to the accompanying drawings and pointed out in the claims. It will be understood that the particular embodiments of the invention are shown by way of illustration and not as limitations of the invention. The principal features of this invention can be employed in various embodiments without departing from the scope of the invention.

The method of the invention includes combining an aqueous solvent medium, in which a lipid membrane and a molecule, which can migrate across the lipid bilayer membrane, are disposed, with a solute. The aqueous solvent medium is suitable for suspending the lipid membrane An example of a suitable aqueous solvent medium is a medium, such as a phosphate-buffer saline solution (hereinafter "PBS solution") having pH of about 7.4, which is suitable for preserving red blood cells. Examples of suitable lipid bilayer membranes include flat, synthetically formed phospholipid membranes, the cell membranes of living cells, isolated cell membranes and vesicles.

The molecule is suitable for migration across the lipid bilayer by the method of the present invention. Examples of suitable molecules include: therapeutic molecules, such as pharmaceutical compounds; peptide; proteins; and cellular components, such as integral membrane proteins and genetic material.

The aqueous medium, having the phospholipid membrane and the molecule disposed therein, can be formed by any suitable method, such as is known in the art of cell culturing. For example, erythrocytes can be isolated by a suitable method, such as that disclosed in Dodge et al., Biochem. Biophys. Acta.:104, pp. 348-354 (1965), the teachings of which are hereby incorporated by reference. The isolated erythrocytes are then separated from a fluid medium in which they are disposed by a suitable method, such as by centrifugation. In one embodiment, the isolated cells are centrifuged in a clinical centrifuge, set at a rate of about 3500 rpms, for about five minutes. The medium is then decanted and the cells are resuspended in a suitable aqueous medium, such as PBS solution. Centrifugation, decanting and suspension are then repeated to further purify the erythrocytes. The purified erythrocytes are then suspended in PBS solution at a concentration of about 1%, by volume.

One embodiment of the method of the invention increases migration of a molecule across a lipid bilayer membrane in the form of a significant reduction of the surfactant concentration and pressure required for lysis of a living cell. In this embodiment, an aqueous solution is prepared which includes a surfactant having a concentration which is sufficient to form micelles of the surfactant during lysis of the living cells, such as erythrocytes, thereby causing migration of a molecule across a lipid bilayer membrane of the erythrocytes. The surfactant is mixed with a suitable aqueous medium, such as PBS solution. In a preferred embodiment, concentration of surfactant in the aqueous medium up to about 0.5 grams/liter. Examples of suitable surfactants include n-octyl β-D-glucopyranoside, Triton-X100 polyethylene glycol-tert-octyl phenyl ehter, commercially available from BioRad Laboratories, Inc.

In a particularly preferred embodiment, the surfactant is dissolved in the medium by the vortexing. The resulting surfactant solution is then mixed with the suspension of erythrocytes described above.

The mixture of the cell suspension and surfactant is then treated at high pressure with a suitable means, such as system 10, shown in FIG. 1. System 10 includes high-pressure gas cell 12. An example of a suitable high-pressure gas cell is a Model No. 2329-800 high-pressure cell, commercially available from Ruska Instrument Corporation. High-pressure cell 12 defines chamber 14 and includes windows 16,18 for allowing a laser beam to pass through high-pressure cell 12 and for detection of laser light transmission through high-pressure cell 12. High-pressure cell 12 also defines inlet port 20 for directing the mixture of the cell suspension and surfactant into chamber 14. Lid 22 is disposed at inlet port 20 for sealing high-pressure cell 12. Vent 24 and high-pressure regulating valve 26 are disposed at high-pressure cell 12 for controlled release of gas pressure within high-pressure cell 12.

Suspension 28 of the cell suspension and surfactant, prepared as described above, is disposed in container 30. Container 30 is suitable for containing suspension 28 of the cell suspension and surfactant. An example of a suitable container is a container formed of a Pyrex glass which is suitable for transmission of laser light employed for measurement of light transmission or light scattering. Container 30 is disposed within high-pressure cell 12.

Conduit 36 extends from gas booster 38 into chamber 14. High-pressure regulating valve 40 is disposed at conduit 36. Gas booster 38 is suitable for pressurizing a solute and delivering the solute through conduit 36 to suspension 28 within container 30 to thereby pressurize suspension 28 and dissolve the solute within suspension 28. Conduit 42 extends between air source 44 and gas booster 38. Conduit 46 extends between gas cylinder 48 and gas booster 38. Gas source 48 contains a solute which is suitable for dissolution in suspension 28 of cells and surfactant in container 30.

An example of a suitable solute is a solute which, during exposure to a sufficient pressure and temperature, dissolves in the aqueous solvent medium of the suspension within container, whereby a significant portion of the dissolved solute migrates to a hydrophobic fatty acyl portion of the lipid bilayer membrane, and thereby allows significantly increased migration of a molecule across the lipid bilayer membrane when a significant portion of the solute is dissolved in the aqueous solvent medium and when a significant portion of the solute is disposed in the hydrophobic fatty acyl portion of the lipid bilayer membrane. An example of a suitable solute is a compound which, at normal temperature and pressure is a hydrophobic gas. A particularly preferred solute is methane.

Suspension 28 of the cell suspension and surfactant described above is directed into container 30 and container 30 is then directed through inlet port 20 into chamber 14. Windows 16,18 of high-pressure cell 12 allow transmission of a laser beam through windows 16,18 and suspension 28 for measurement of laser light transmission through the suspension. Lid 22 is then closed to seal suspension 28 within chamber 14.

Laser 50 is aligned with windows 16,18 of high-pressure cell 12 and is suitable for directing laser beam 52 through windows 16,18 to thereby measure changes in light transmission across suspension 28 in container 30 when suspension 28 is at an elevated pressure. The changes in light transmission measure differences in turbidity of suspension 28 and thereby enable identification of the size and/or concentration of particles in suspension 28. An example of a suitable laser is a 10 mW He-Ne random polarization laser. Preferably, laser 50 is aligned for directing laser beam 52 at a normal angle of incidence to windows 16,18. Photodetector 54 is aligned with laser beam 52 and windows 16,18 for detecting transmission of laser beam 52 through suspension 28 within container 30. Alternatively, a photodiode or photomultiplier can be employed to detect the transmission of laser beam 52 through suspension 28.

The temperature of suspension 28 in container 30 is controlled by temperature-control means 56. Temperature control means 56 includes, for example, heating tape 58, such as thermolyn heating tape, commercially available from Fisher Scientific, which is disposed about high-pressure cell 12. Temperature control means 56 also includes variable auto transformer 60, which is connected to heating tape 58 by wires 62,64.

The temperature of suspension 28 is established by activating the temperature control means 56. For most embodiments, the temperature is in the range of between about 0° C. and about 60° C.

High-pressure cell 12 is then flushed with the solute by directing solute gas from gas source 48 through conduit 46 and then pressurizing the gas at gas booster 38 to a pressure in the range of between about 0.5 and about 5 MPa. High-pressure regulating valve 40 is then opened and pressurized gas is directed from gas booster 38 through conduit 36 and valve 40 into chamber 14 to thereby pressurize high-pressure cell 12 to a pressure in the range of between about 0.25 and about 2.5 MPa.

In one embodiment, high-pressure cell 12 is flushed with solute gas. The procedure includes pressurizing high-pressure cell 12 in increments of about five MPa and maintaining that pressure. After a suitable period of time, which is sufficient for substantial equilibration of the solute gas in chamber 14, the pressure within the chamber 14 is released by opening valve 26 in an amount sufficient to reduce the pressure to atmospheric over a period of between about two and three minutes. High-pressure cell 12 is then flushed with solute gas in the same manner two or three more times in order to purge essentially all air and moisture from chamber 14.

A significant portion of the erythrocyte cells in suspension 28 are then lysed by pressurizing chamber 14 with solute gas in an amount sufficient to cause a significant portion of the solute gas to dissolve in suspension 28, whereby the solute gas migrates to the hydrophobic core of the erythrocyte bilayer. The pressure in chamber 14 is increased in increments of about ten MPa and at intervals of about two minutes until the partial pressure of solute gas in the chamber 14 is in the range of between about twenty and about three hundred MPa. The lipid bilayer of the erythrocyte cells in suspension 28 dissolves, thereby allowing components of the cells, such as hemoglobin, to be released into the aqueous medium of the suspension.

The migration of the solute, which is methane in this embodiment, to the hydrophobic fatty acyl portion of the lipid bilayer membrane of the erythrocyte cells causes the cells to lyse at a temperature and pressure, and at a concentration of surfactant in the suspension, which are significantly lower than that which is required to lyse the cells without the presence of solute in suspension 28. In other words, the concentration of surfactant required to lyse a significant portion of the erythrocytes is significantly lowered with increasing methane pressure by the method of this invention.

The migration of the solute to the hydrophobic fatty acyl portion of the lipid bilayer membranes of the cells thereby allows significant transport of molecular components across the lipid bilayer membrane. In this embodiment, the transport of the molecular component across the lipid bilayer membrane is significantly increased by significantly lowering the concentration of surfactant required to lyse the cells and at a desired temperature and pressure, whereby molecular components, such as hemoglobin and membrane components, are released from the cells or from the lipid bilayer membranes by rupture of the membranes.

High-pressure cell 12 is then depressurized, after the incubation period is over, by opening needle valve 26 and allowing the gas within high-pressure cell 12 to escape through vent 24 over a period of time in the range of between about one and one and one-half hours until the pressure within high-pressure cell 12 is about atmospheric. The solute volatilizes and dissipates from suspension 28, whereby essentially no solute remains within suspension 28 upon completing depressurization of high-pressure cell 12.

High-pressure cell 12 is then opened and container 30 is removed from high-pressure cell 12. Suspension 28 can then be treated by suitable means to determine the amount of erythrocyte lysis which occurred during exposure of suspension 28 to the solute within the high-pressure cell 12.

The method of the present invention allows significantly increased migration of a molecule across a lipid bilayer membrane. It is to be understood that the lipid bilayer membrane can be, for example, a micelle, a vesicle, a cell membrane, etc. It is also to be understood that migration across the lipid bilayer membrane can occur in any of several different forms, such as: release of a molecule which is entrapped within the lipid bilayer membrane; rupture or lysis of the lipid bilayer membrane, as in lysis of a living cell, which releases molecules contained within the cell; migration of a molecule across a lipid bilayer membrane from one side of the membrane to another side of the membrane without rupture of the membrane; fusion of lipid bilayer membranes, whereby a molecule entrapped by one lipid bilayer membrane becomes entrapped within a second lipid bilayer membrane by fusion of the membranes to form a single lipid bilayer membrane; migration of a molecule enclosed within a vesicle across a lipid bilayer membrane of the vesicle and across a lipid bilayer membrane of a living cell to thereby deliver the molecule from the vesicle to within the cell; migration of a molecule enclosed within a living cell across a cell membrane of the living cell and across a lipid bilayer of a vesicle to thereby deliver the molecule from the living cell to the vesicle; migration from a micelle and across a lipid bilayer of a vesicle or a cell membrane of a living cell; etc.

In addition, it is to be understood that increased migration of a molecule across a lipid bilayer membrane can have several alternative forms. For example, migration of a molecule across a lipid bilayer can be significantly increased by significantly reducing the concentration of surfactants required to cause lysis of a cell, or by significantly reducing the pressure required for lysis of a cell at a given surfactant concentration. Also, increased migration of a molecule can be in the form of reducing the size of micelles formed during cell lysis at a constant surfactant concentration.

In one alternative embodiment of the method, two lipid bilayers are included. One lipid bilayer is a vesicle and the other is the cell membrane of a living cell. The molecule is disposed within the vesicle. The vesicle and the living cell are disposed in a suitable aqueous medium. The vesicle, the living cell and the aqueous medium are then exposed to a solute which, during exposure to sufficient pressure and temperature, substantially dissolves in the aqueous medium. A significant portion of the dissolved solute migrates to a hydrophobic fatty acyl portion of the lipid bilayers of both the vesicle and the living cell. The aqueous solvent medium, the vesicle, the living cell and the solute are then exposed to a temperature and pressure sufficient to substantially dissolve in the aqueous medium, whereby the solute migrates from the aqueous medium to the hydrophobic fatty acyl portion of the cell membrane of both the vesicle and the living cell, thereby allowing migration of the molecule from the vesicle and across the cell of the living cell. In one embodiment of this alternative, the molecule in the vesicle migrates from the vesicle to the living cell by causing the vesicle and the cell membrane of the living cell to fuse.

In another embodiment of the method of the present invention, a living cell and nucleic acids are included. The living cell is disposed in a medium suitable for sustaining the growth of the cell. Nucleic acid of suitable concentration in a suitable buffer is added to the living cell disposed in the medium and are then exposed to a solute, which during exposure to sufficient pressure and temperature, substantially dissolves in the medium. Exposure of the medium, the cell and the nucleic acids to sufficient pressure and temperature causes the solute to substantially dissolve in the medium, whereby a significant portion of the solute migrates to the hydrophobic fatty acyl portion of the membrane of the living cell, thereby allowing significantly increased migration of the nucleic acids across the membrane and into the interior of the cell. The nucleic acids thereby modify the cell in such a way that the cell acquires properties which are dictated by the nucleic acids.

The significantly increased migration of nucleic acids from the medium to the interior of the living cell can be monitored, for example, by growing the modified cells in a selective medium which allows growth of only the modified cells. In addition to significantly increasing migration of nucleic acids across cell membranes into cells, this procedure can be used to introduce foreign, as well as extra-genetic, material into living cells.

In still another embodiment of the invention, a system for analyzing a molecule by high-pressure liquid chromatography includes a high-pressure vessel. A container is disposed within the high-pressure vessel for containing an aqueous solvent having a lipid bilayer and a molecule disposed therein. The system also includes suitable means for pressurizing the reaction vessel with a solute. The solute, at sufficient partial pressure, dissolves in an aqueous solvent contained in the container, whereby a significant portion of the solute migrates to a hydrophobic fatty acyl portion of the lipid bilayer membrane disposed in the aqueous solvent. The pressurizing means can also pressurize the solute and the aqueous solvent in the reaction vessel to a partial pressure of the solute which is sufficient to cause the solute to dissolve in the aqueous solvent in an amount sufficient to cause the molecule in the container to migrate across the liquid bilayer membrane. Suitable means separate the molecule from the lipid bilayer membrane. Chromatographic means identify the separated molecule, thereby analyzing the molecule.

The invention will now be further and specifically described by the following examples. All parts and percentages are by weight unless otherwise stated.

EXAMPLE I

Materials: Triton X-100 polyethylene glycol-tert-octyl phenyl ether was obtained from BioRad Laboratories, Inc. and n-octyl $\beta$-D-glucopyranoside, having a minimum priority of about 98% was obtained from Sigma Chemical Co., Inc. A Model #2329-800 high-pressure cell was obtained from Ruska Instrument Corp., Inc. and modified as shown in FIG. 1. Methane and nitrogen were employed as solutes. The purity of methane and nitrogen used was 99.00%.

Peripheral whole blood was drawn and collected in a Vacutainer evacuated blood collection tube, commercially available from Fisher Scientific, Inc., containing lithium heparin as an anticoagulant. Erythrocytes from the whole blood were isolated as described by Dodge et al., *Biochem. Biophys Acta.*:104, pp. 348-354 (1965). The erythrocytes were centrifuged at 3,5000 rpm for three minutes in a clinical centrifuge and the resulting supernatant plasma was removed by Pasteur pipet. Pelletized erythrocyte cells were then resuspended in phosphate buffer saline (PBS) (pH 7.4) and centrifuged as above. Buffy coat and supernatant were removed and the process was repeated five times to separate white blood cells and platelets from the erythrocytes. The erythrocytes were finally suspended in phosphate buffer saline (pH 7.4) and stored in a refrigerator at a temperature of about four degrees Celsius. Isolated erythrocytes were used for twenty-one days, after which they were discarded and a fresh preparation was made in the same way.

An aliquot of 5 ml erythrocyte suspension was drawn from the stock, centrifuged at 3,500 rpm for three minutes, and, from the pelletized erythrocytes, 0.5 ml were pipetted into a test tube and diluted with 49.5 ml of phosphate buffer saline (pH 7.4) to give a 1% erythrocyte suspension. This 1% erythrocyte suspension had approximately $1.2235 \times 10^8$ cells per ml. Similarly, a 1% erythrocyte suspension was prepared in Alsever's buffer (pH 6.4). All experiments were performed using 1% erythrocyte in the required buffer.

Increasing amounts of a solution of n-octyl $\beta$-D-glucopyranoside (10% w/v) were added to aliquots of erythrocyte suspension and gently mixed. These cell suspensions were then disposed in high-pressure cell 12. High-pressure cell 12 was then sealed. High-pressure cell 12 was then pressurized with the gas. Gas pressure was increased in small increments of approximately 10 MPa, each time, and about two minutes was allowed for each equilibration. After the desired gas pressure was achieved, needle valve 40 was closed and the erythrocyte suspension was held at that pressure. A similar set of erythrocyte suspensions were kept at room temperature 22° C., and at atmospheric pressure as a control. After 10 hours of incubation, high-pressure cell 12 was depressurized by first equilibrating the pressure in the gas booster with the pressure in high-pressure cell 12. Needle valve 40 was then opened, followed by slowly opening valve 26.

After depressurization, all samples (control and pressurized) were centrifuged, to thereby pelletize the erythrocytes, in Eppendorf tubes at 3,500 rpm for five minutes. Supernatant was removed and marked "S". The pelleted erythrocytes were lysed by adding water to a final volume of one ml, which was marked "P". The supernatant "S" was also diluted to a final volume of one ml. The lysed erythrocyte solutions "P", were centrifuged at 13,500 rpm for thirty minutes to pelletize the membranes.

Overall, the method was performed on suspensions having concentrations of 0, 0.10, 0.15, 0.20, 0.25, 0.30, 0.35, 0.40, and 0.45% of n-octyl $\beta$-D-glucopyranoside at 20, 41, 64, MPa at 22° C. A similar set of experiments were completed using Triton X-100 polyethylene glycol-tert-octyl phenyl ether. The only difference in the procedure, wherein Triton X-100 polyethylene glycol-tert-octyl phenyl ether solution was employed, was that the stock solution of Triton X-100 polyethylene glycol-tert-octyl phenyl ether was 0.2% in phosphate buffer saline (pH 7.4) and that the final concentrations of Triton X-100 polyethylene glycol-tert-octyl phenyl ether in the erythrocyte suspensions were 0.0005, 0.001, 0.002, 0.003, 0.004, 0.005, 0.006, 0.007, 0.008%.

Percent Erythrocyte survival: Each supernatant and lysate was diluted to a final volume of one ml with water. From this 1 ml of supernatant or lysate solution, 0.3 ml aliquot was taken and diluted to three ml with water and the absorbance at 414 nm was measured on a Hewlett Packard Diode Array Spectrophotometer, Model HP8451A. Erythrocyte survival was calculated using the following formula for each sample:

% Hemolysis = 100 (S/(S+P))
% Erythrocyte survival = 100 − % hemolysis where "S" is the total supernatant absorbance and "P" is total pellet absorbance at 414 nanometers.

Results

Figure 2:
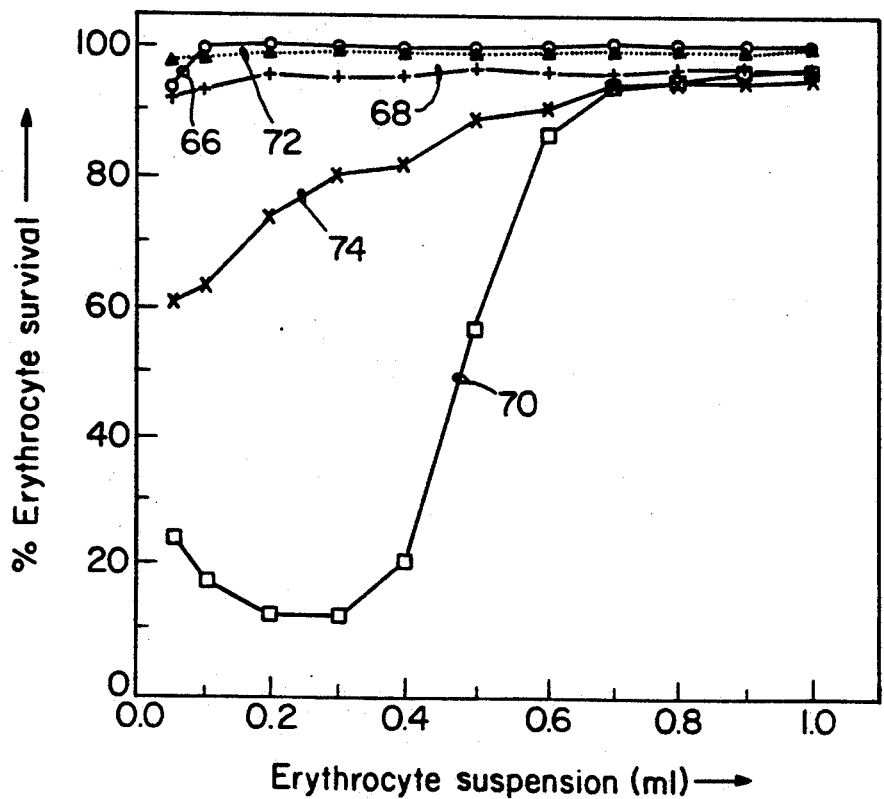
FIG. 2 is a plot of erythrocyte survival at various pressures in different volumes of buffer solutions at 22° C. and employing either methane or nitrogen as a solute according to the method of the invention.

Volume and buffer-dependent percent erythrocyte survival is shown in FIG. 2. Percent erythrocyte survival in phosphate buffer saline (pH 7.4) is shown at: one atmosphere (0.1 MPa) (Curve 66); 64 MPa nitrogen (Curve 68); 64 MPa methane (Curve 70). Percent erythrocyte survival is also shown in Alsever's buffer (pH 6.4) at: one atmosphere (0.1 MPa) (Curve 72); and 64 MPa methane (Curve 74). Erythrocyte survival in both cases was plotted for increasing volumes of: 0.050, 0.1, 0.2, 0.3, 0.4, 0.5, 0.6, 0.7, 0.8, 0.9, and 1 ml.

These plots indicate three points. First, more than 95% of the erythrocyte survived in phosphate buffer saline (pH 7.4) (Curve 66) and in the Alsever's buffer (pH 6.4) (Curve 72) at one atmosphere. Second, in phosphate buffer saline (pH 7.4) at 64 MPa nitrogen (Curve 68), erythrocyte survival was similar to the control at one atmosphere (Curve 66). Third, erythrocyte survival in phosphate buffer saline (pH 7.4) at 64 MPa methane (Curve 70) changed with volume. For example, it decreased from 0.50 to 0.3 ml and increased from 0.3 to 1 ml. Further, for Alsever's buffer pH 6.4 at 64 MPa methane (Curve 74), erythrocyte survival increased from about 60 to about 90%.

Thus, Alsever's buffer (pH 6.4) protected erythrocytes from lysis when subjected to 64 MPa methane (Curve 74). As a result of increasing volume in Curve 70, the concentration of solubilized methane decreased, thus decreasing the solute effect with increasing cell suspension volume. When the maximum concentration of methane as a solute was 0.3 ml, and the incubation period was ten hours at 64 MPa, as shown in Curve 70, and beyond 0.6 ml, the solute "methane" is present in small quantities so as not to hemolyze the erythrocytes. From these results it was clear to chose 0.3 ml as a working volume for all pressure experiments and the incubation time 10 hours or more. Curve 70 in FIG. 2 further indicates that at 0.3 ml volume maximum solute "methane" is soluble in the phosphate buffer saline (pH 7.4) and that the solute "methane" further partitions in to the hydrophobic fatty acyl region of the cell membrane, thereby causing a surfactant-like action resulting in hemolysis of the cell.

Figure 3:
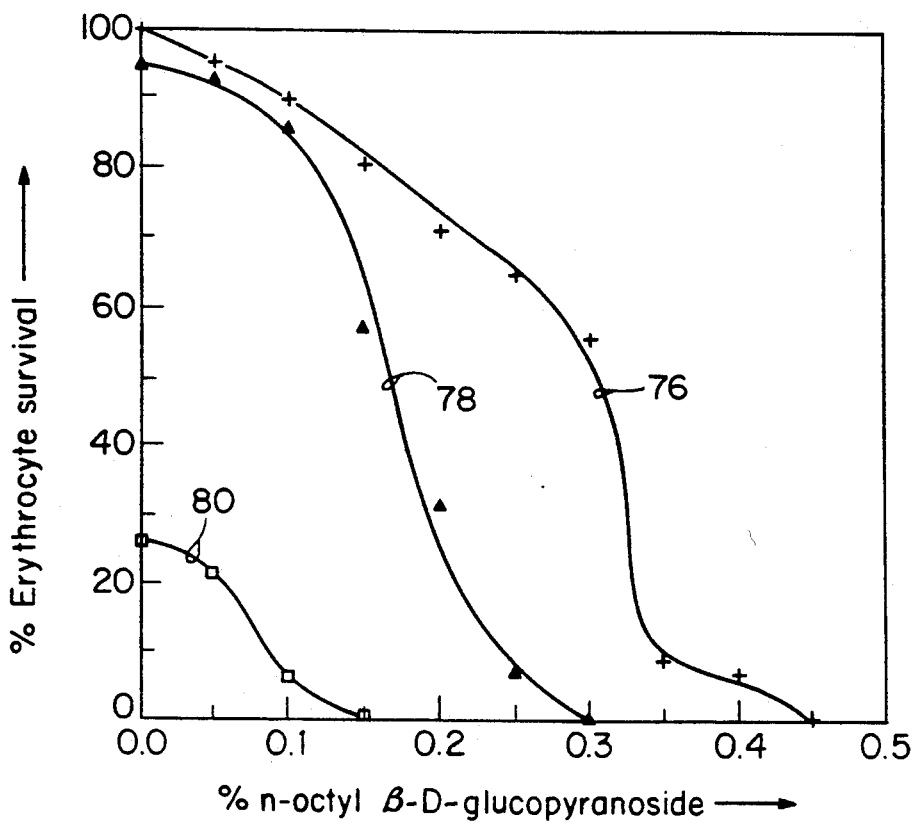
FIG. 3 is a plot of erythrocyte survival at various pressures in a buffer solution, containing various amounts of n-octyl β-D-glucopyranoside, at 22° C. and employing methane as a solute according to the method of the invention.

FIG. 3 further details the erythrocyte survival in phosphate buffer saline for 0.3 and one ml in the presence of 0.00, 0.05, 0.1, 0.15, 0.2, 0.25, 0.3, 0.35, 0.4, and 0.45% n-octyl $\beta$-D-glucopyranoside. Curve 76 is a plot of erythrocyte survival of a control suspension at one atmosphere (0.1 MPa), Curve 78 is a plot of erythrocyte survival in 1 ml of erythrocyte suspension at 64 MPa methane and Curve 80 is a plot of erythrocyte survival in 0.3 ml erythrocyte suspension at a partial pressure of methane of 64 MPa. The incubation period for Curves 76,78 and 80 was kept at twelve hours and the temperature was maintained at 22° C. FIG. 3 shows that the percent erythrocyte survival is much higher in a one ml suspension at 64 MPa methane (Curve 78) at various concentrations of n-octyl $\beta$-D-glucopyranoside, than is shown by Curve 80. Thus, at a lower volume, 0.3 ml of suspension, a significant portion of the solute is dissolved into the aqueous medium and acts on the cell membrane in conjunction with the n-octyl $\beta$-D-glucopyranoside. Essentially, complete hemolysis of cells was thereby caused at 0.15% n-octyl $\beta$-D-glucopyranoside concentration, as compared to 0.3% of n-octyl $\beta$-D-glycopyranoside concentration required in the case of one ml erythrocyte suspension was kept at the same pressure for the same period of time.

Figure 4:
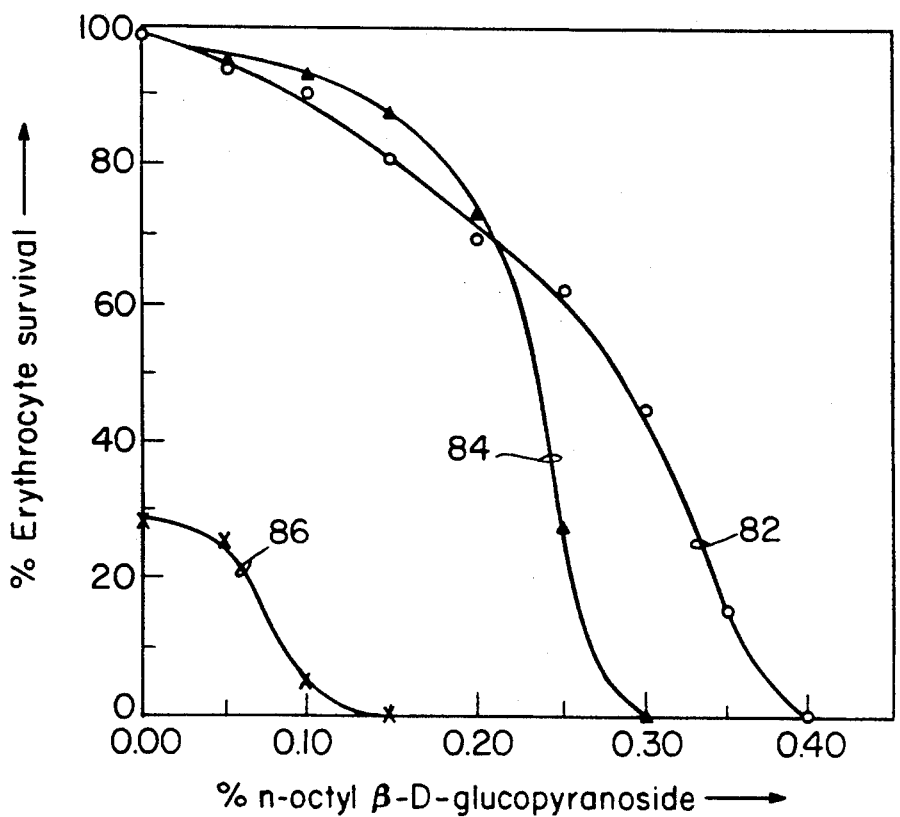
FIG. 4 is a plot of erythrocyte survival in a buffer solution, containing various amounts of n-octyl β-D-glucopyranoside, at 64 MPa, and employing methane or nitrogen as solutes according to the method of the invention.

FIG. 4 is a plot of percent erythrocyte survival for: a control suspension one atmosphere (Curve 82); 64 MPa methane (Curve 86); and 64 MPa nitrogen (Curve 84) of a 0.3 ml erythrocyte suspension in phosphate buffer saline (pH 7.4) incubated for a period of twelve hours at 22° C. As can be seen in FIG. 4, the solute, methane, when dissolved at 64 MPa in the cell suspension in phosphate buffer saline pH 7.4 had a significantly increased detergent-like activity (Curve 86) as compared to nitrogen (Curve 84) when dissolved at the same pressure 64 MPa under the same conditions. Therefore, methane had a significantly greater effect on the lysis of cells by migration into the erythrocyte membrane hydrophobic region. Another interesting phenomena observed in FIG. 4 was the protection effect of nitrogen on erythrocytes (Curve 84), at lower concentrations of n-octyl $\beta$-D-glucopyranoside 0.05, 0.1, 0.15, and 0.2, as compared to the control (Curve 82).

Figure 5:
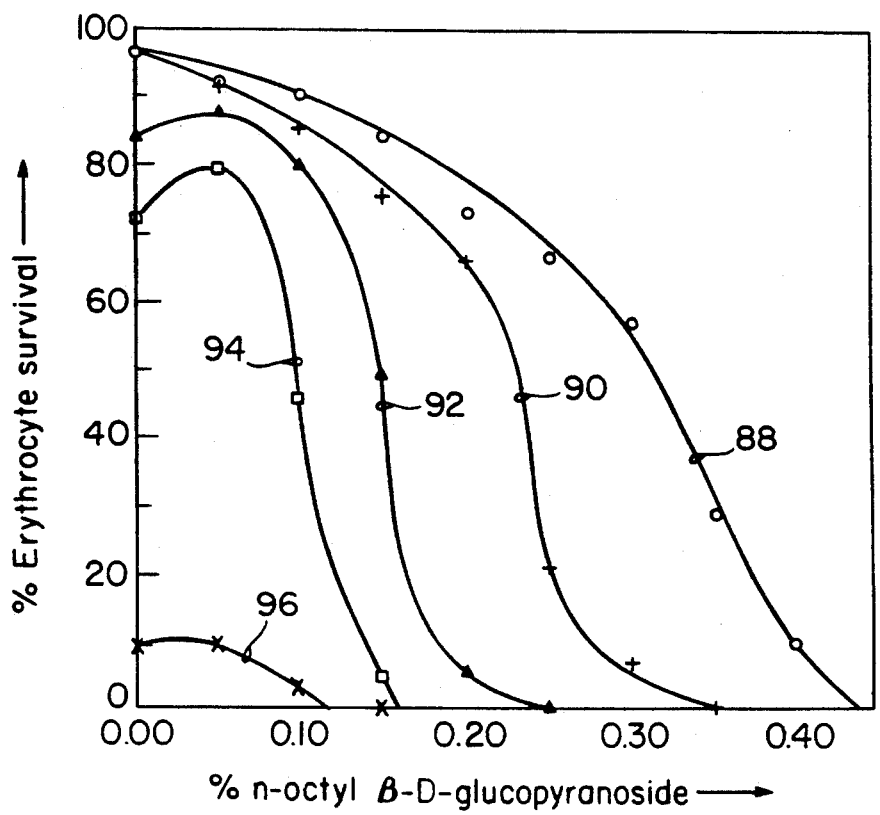
FIG. 5 is a plot of erythrocyte survival in a buffer solution, containing various amounts of n-octyl β-D-glucopyranoside, at various pressures and employing methane as the solute according to the method of the invention.

Experiments were done using 0.3 ml of a 1% erythrocyte suspension in phosphate buffer saline (pH 7.4) with increasing concentrations of n-octyl $\beta$-D-glucopyranoside, 0.00, 0.05, 0.1, 0.15, 0.2, 0.25, 0.3, 0.35, 0.4, 0.45, at one atmosphere and at 20, 41, 50 and 64 MPa of methane. Plots of percent erythrocyte survival of control kept at: one atmosphere (0.1 MPa) Curve 88; at 20 MPa methane Curve 90; at 41 MPa methane Curve 92; at 50 MPa methane Curve 94; and at 64 MPa methane Curve 96, are shown in FIG. 5. With significant increase in methane pressure, which means significant increase in concentration of methane as a solute in the erythrocyte cell suspension, the percent erythrocyte survival dropped, as seen in Curves 90 through Curve 96.

As can be seen in the curves, an inward trend of the curves with increasing pressure, suggests that significantly increased concentrations of the solute were dissolved as the pressure increased from 20 to 64 MPa. Significantly increased migration of the methane into the erythrocyte membrane thus causes significantly increased hemolysis, such as at the highest pressure under study, 64 MPa. Another important observation noted in FIG. 5, was at zero detergent concentration of n-octyl $\beta$-D-glucopyranoside, which shows that at 64 MPa methane, erythrocyte lysis was 90%, whereas, at 50 MPa methane, erythrocyte lysis was 30%. This indicated that, with an increase in pressure from 50 to 64 MPa, the additional dissolved solute caused a chaotic effect on the erythrocyte membrane, which resulted in cell lysis.

Figure 6:
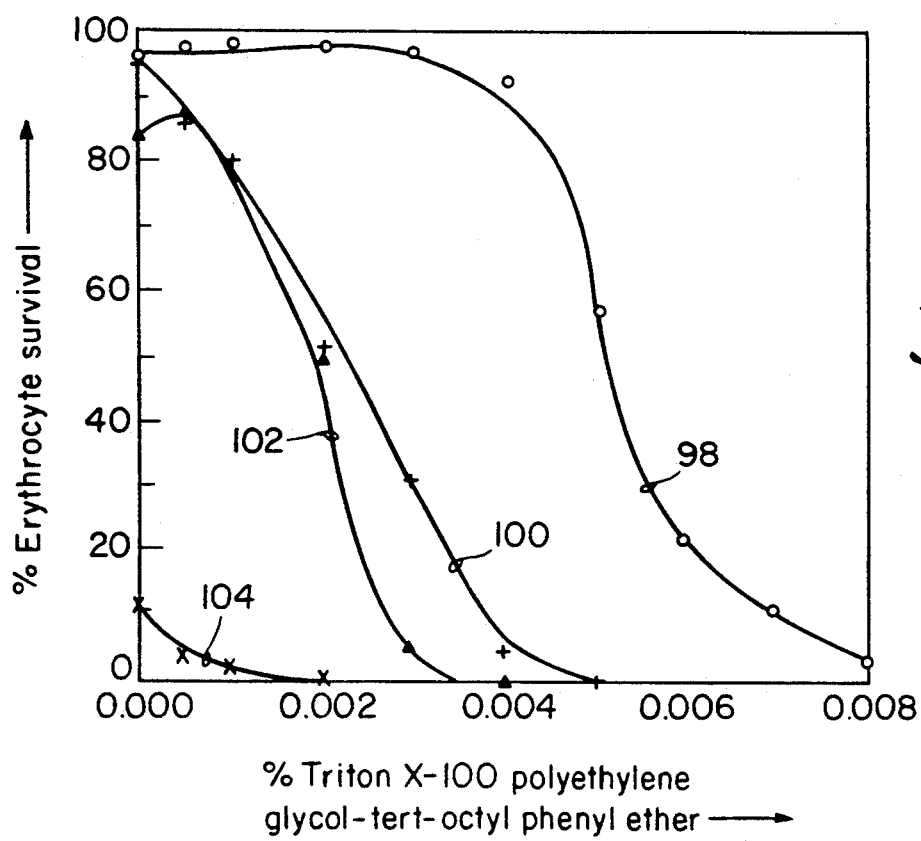
FIG. 6 is a plot of erythrocyte survival in a buffer solution, containing various amounts of Triton X-100 polyethylene glycol-tert-octyl phenyl ether, at various pressures and employing methane as the solute according to the method of the invention.

A similar experiment was performed using Triton X-100 polyethylene glycol-tert-octyl phenyl ether as the detergent, as shown in FIG. 6. Percent erythrocyte survival is shown for: a control at one atmosphere (0.1 MPa) (Curve 98); at 20 MPa methane (Curve 100); at 41 MPa methane (Curve 102); and at 64 MPa methane curve 104. The results and interpretation from this graph are consistent with the results previously discussed for FIG. 5, and hence are not repeated here.

Figure 7:
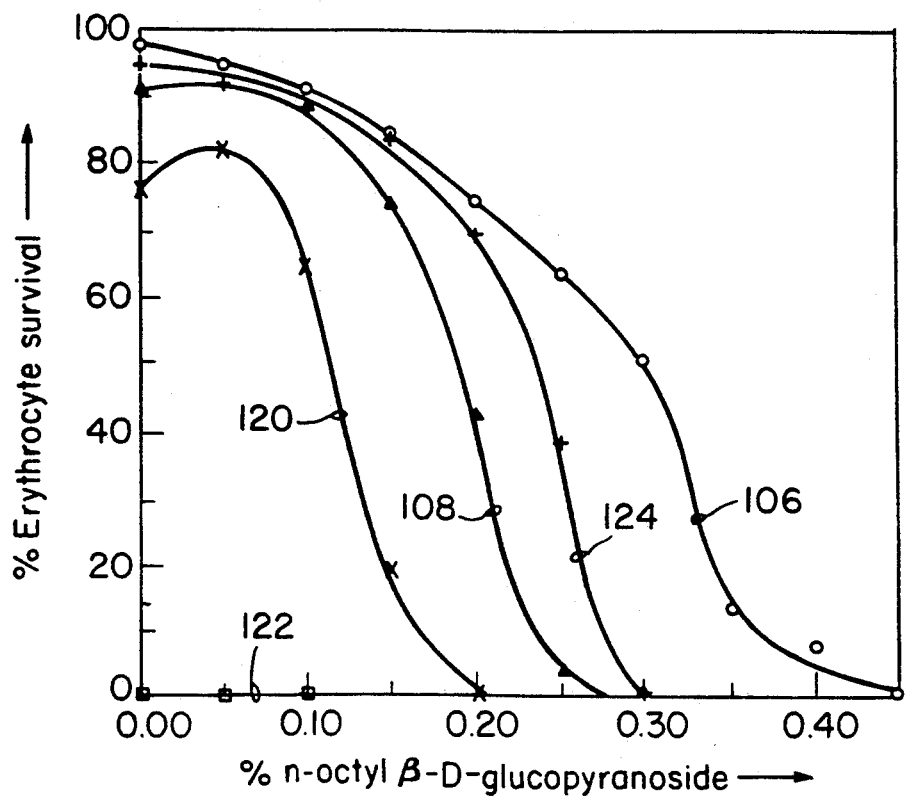
FIG. 7 is a plot of erythrocyte survival in a buffer solution, containing various amounts of n-octyl β-D-glucopyranoside, at various pressures and employing methane or nitrogen as the solute according to the method of the invention.

Experiments were performed to further support the data of high pressure requirements to cause significantly increased hemolysis of erythrocytes. Erythrocytes suspended in phosphate buffer saline (pH 7.4), with increasing concentrations of n-octyl $\beta$-D-glucopyranoside, were kept for an extended period of time, twenty-four hours, at: one atmosphere; 20; 41; and 64 MPa methane, and at 64 MPa nitrogen. The results of these experiments are shown in FIG. 7. The percent of erythrocyte survival for each concentration is shown in FIG. 7 at: one atmosphere (0.1 MPa) as a control (Curve 106); at 20 MPa methane (Curve 108); at 41 MPa methane (Curve 120); at 64 MPa methane (Curve 122); and at 64 MPa nitrogen (Curve 124).

The interpretation of FIG. 7 can be subdivided into two parts:

(i) the incubation period for Curves 106, 108, 120, 122 and 124 Was twenty-four hours, which means that the effect of dissolved solute on erythrocytes in this experiment was for a relatively extended period of time, wherein the effect caused by the solute was forced to completion. This, in other words, can be explained as: at the given pressure, the solute dissolved in the erythrocyte suspension remained for an extended period of twenty-four hours, where it had an opportunity to migrate into the bilayer and cause a lytic effect during this period. The control in FIG. 7 (Curve 106) did not differ much from the control in FIG. 5 (Curve 88) where the former was incubated for twenty-four hours and the latter for twelve hours. There was a small difference in the hemolysis effect with an increase in incubation period of twenty-four hours for methane pressures of 20 MPa (Curve 108), 41 MPa (Curve 120) and 64 MPa (Curve 122) in FIG. 7, as compared to erythrocytes incubated for twelve hours at the same pressures in FIG. 5 (Curves 90, 92 and 96), respectively. Erythrocyte survival at 64 MPa nitrogen, FIG. 7 (Curve 124), having an incubation period twenty-four hours, was nearly identical to that observed for twelve hours, FIG. 4 (Curve 84). Thus, this demonstrates that higher incubation periods did not significantly change the hemolysis behavior. That is to say, methane pressure at 41 MPa for twenty-four hours did not have the same effect as methane pressure at 64 MPa for 12 hours, which means that, for a given solute, the effect observed on bilayer membrane could be observed only by having the required amount of solute in the solution which corresponds to the required amount of pressure. In other words, no effect would be observed at lower pressures, however long the incubation period was extended.

(ii) Nitrogen behaved as the control. No significant effects of nitrogen were observed when erythrocyte suspensions were kept under nitrogen pressure of 64 MPa for twelve hours, FIG. 4 (Curve 84), or for twenty-four hours, FIG. 7 (Curve 124). This further demonstrates that, for the solute to dissolve and have an effect on the erythrocyte membrane or, in general, a bilayer system, the required solute system should be present in an appropriate concentration for an optimum period in the given buffer, to dissolve and migrate into the system under consideration.

Figure 8:
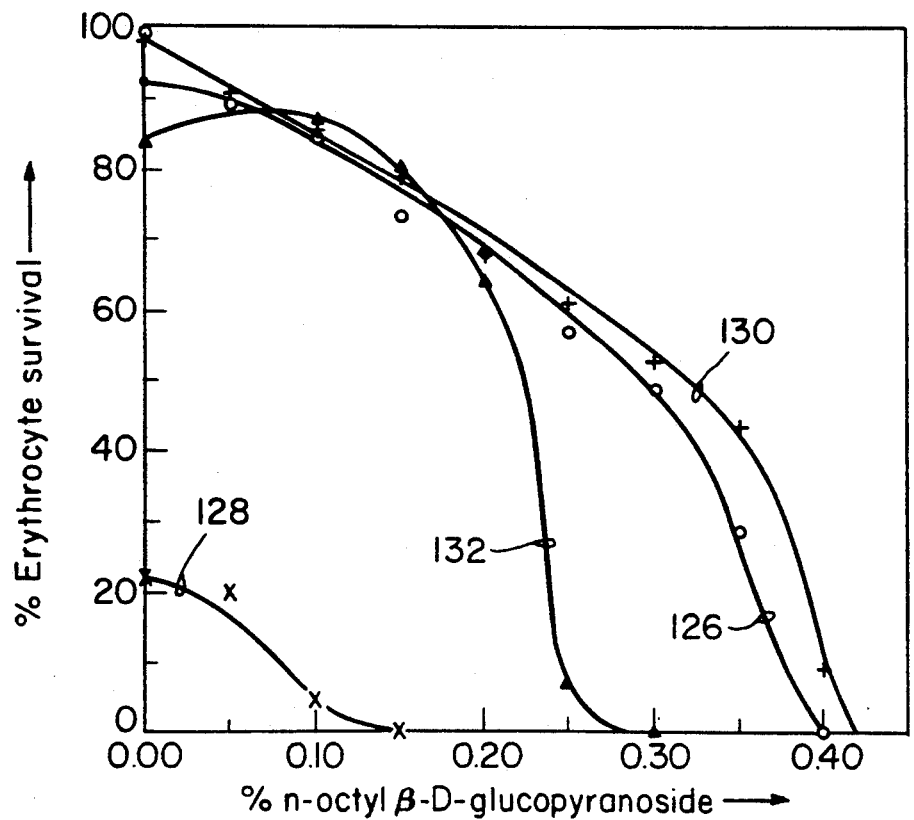
FIG. 8 is a plot of erythrocyte survival in a buffer solution, containing various amounts of n-octyl β-D-glucopyranoside, wherein the buffer solution is either a phosphate buffer or Alsevar's buffer, and employing methane as the solute.

Erythrocyte survival behavior has further been studied for methane pressures in other buffer systems, namely in Alsever's buffer (pH 6.4), and plots of erythrocyte survival at one atmosphere in phosphate buffer saline (pH 7.4), are shown in FIG. 8 (Curve 130) and at 64 MPa methane (Curve 132). Buffer constituents clearly played an important role in the erythrocyte survival, as seen from FIG. 8, discussed above. Alsever's buffer (pH 6.4) had a protective effect on erythrocytes, as seen from Curve 132, FIG. 8, where, as in phosphate buffer saline (pH 7.4) methane pressure of 64 MPa had a significant effect on the hemolysis. This meant that the solute methane, which dissolved in Alsever's buffer, did not exert the same solute effect as in case of phosphate buffer solution (pH 7.4). Hence, the buffer constituents were an important factor in these high-pressure experiments.

Therefore, in an appropriate buffer system, at least a portion of the solute methane which dissolved as a result of pressure migrated into the erythrocyte membranes in a concentration which was directly related to the pressure used and, when incubated for an optimum amount of time, the solute "methane" had a detergent-like action which caused lysis of the cell, thereby indicating that methane can be employed as a membrane-active reagent. This system can be applied in general to any bilayer membrane.

EXAMPLE II

Aliquots of 500 μl of erythrocyte suspension (20% in Alsever's buffer) were mixed and incubated with 500 μl of L-α-dipalmitoly phosphatidylcholine vesicles ("DPPC"), at concentrations of 0, 5, 10, and 20 μmol/ml in Alsever's buffer (pH 6.4). One set of the erythrocyte/vesicle suspensions was incubated at one atmosphere and another set was incubated at 64 MPa methane for five hours. Depressurization was done as described above and the cells were separated from the erythrocyte-vesicle solution by centrifugation at 3500 rpm for three minutes. The supernatant was separated and saved, and the cells were washed with 500 μl of Alsever's buffer (pH 6.4) and centrifuged as before. Supernatant containing traces of lipid vesicles was combined with the earlier supernatant and dilipidated with 2:1 chloroform:methanol (v/v). The aqueous phase was concentrated and a SDS-PAGE analysis was used.

At 20° C. and at one atmosphere, the erythrocytes did not show any protein exchange into the vesicle phase. Also, at nitrogen pressure of 64 MPa and at 22° C., no significant amount of proteins were extracted from the erythrocyte membranes. Erythrocytes incubated with increasing lipid vesicles concentrations at 22° C., 64 MPa methane showed significant amounts of proteins extracted, as detected by SDS-PAGE.

Figure 9A:
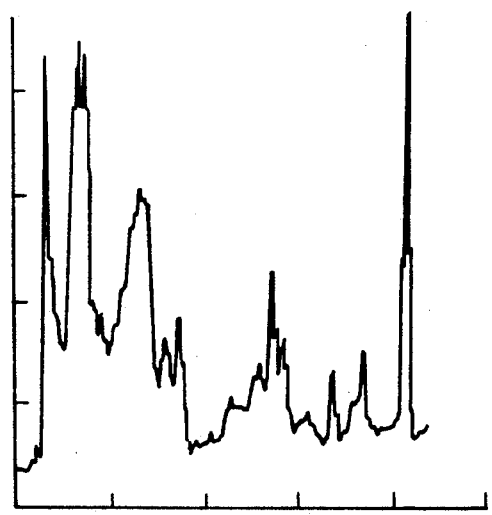
FIG. 9 is a series of plots of densitometric traces of erythrocyte membrane proteins isolated by the method of the invention.
Figure 9B:
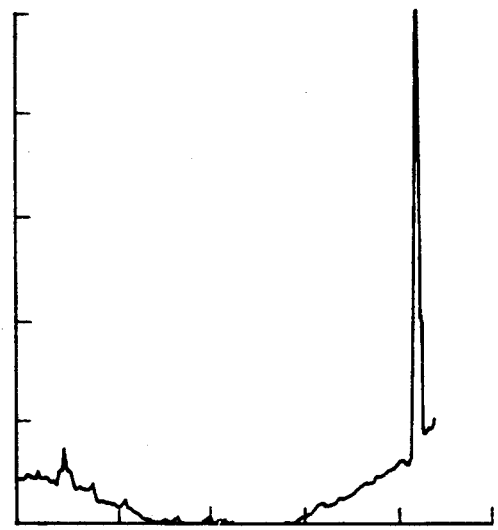
Figure 9C:
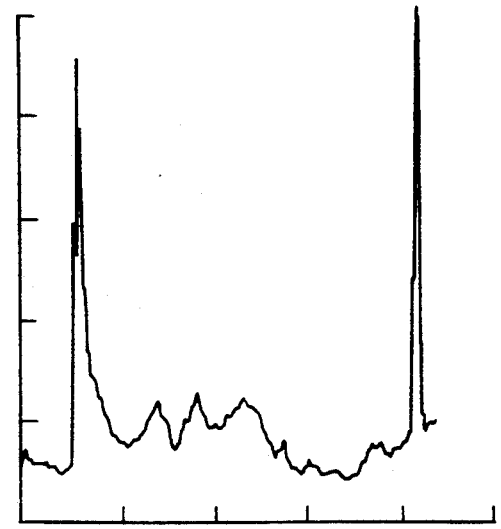

FIG. 9 shows densitometric traces from three lanes of an SDS-PAGE gel. Lane "A" represents isolated erythrocyte membrane protein pattern. Lane "B" was a control at one atmosphere (0.1 MPa). Erythrocytes were incubated with 20 μmol/ml DPPC vesicle solution, where essentially no proteins were seen on the gel. This is similar to what was observed when erythrocytes with same lipid concentration were incubated at 64 MPa nitrogen at 22° C. Lane "C" was a similar sample kept at 64 MPa methane.

The proteins detected were co-isolated with the lipid vesicles. A large portion of the proteins isolated in the vesicle phase under methane pressure were in a tightly aggregated state and hence unable to resolve on the gel. The major integral membrane protein, the anion transporter (band 3), was distinctly co-isolated in the vesicles, along with other membrane proteins from the erythrocyte membrane. Spectrin, the major cytoskeletal component, was not extracted by the lipid vesicles, which indicated that only the membrane proteins were exchanged as a result of methane pressure.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method for causing increased migration of a molecule across a lipid bilayer membrane, comprising the steps of:
    a) combining an aqueous solvent medium, in which the lipid bilayer membrane and a molecule, which can migrate across the lipid bilayer membrane, are disposed, with a solute which, at a sufficient partial pressure of the solute, dissolves in the aqueous solvent medium, a portion of the dissolved solute migrating to a hydrophobic fatty acyl portion of the lipid bilayer membrane, and which causes increased migration of the molecule across the lipid bilayer membrane when a portion of the solute is dissolved in the aqueous solvent medium and when a portion of the solute is disposed in the hydrophobic fatty acyl portion of the lipid bilayer membrane; and exposing the aqueous solvent medium and the lipid bilayer membrane to a sufficient partial pressure of the solute to cause the solute to dissolve in the aqueous solvent medium, whereby a portion of the solute migrates to the hydrophobic fatty acyl portion of the lipid bilayer membrane, thereby causing increased migration of the molecule across the lipid bilayer membrane.

2. A method of claim 1 wherein the molecule becomes incorporated into the lipid bilayer.

3. A method of claim 1 wherein the molecule migrates through the lipid bilayer.

4. A method of claim 3 wherein the molecule is a therapeutic molecule.

5. A method of claim 3 wherein the molecule is a peptide.

6. A method of claim 3 wherein the molecule is a nucleic

7. A method of claim 3 wherein the molecule is a protein.

8. A method of claim 7 wherein the molecule is an integral membrane protein which is disposed in the lipid bilayer and which migrates across the lipid bilayer into the aqueous medium.

9. A method of claim 8 further including the step of combining the aqueous medium with a surfactant, the surfactant having a concentration sufficient to form a micelle which includes the integral membrane protein.

10. A method of claim 9 wherein the partial pressure of the solute to which the aqueous solvent medium, the surfactant and the lipid bilayer are exposed is sufficient to diminish the critical micelle concentration of the surfactant in the aqueous medium.

11. A method of claim 1 wherein the lipid bilayer is a component of a vesicle and wherein the molecule migrates from the vesicle, across the aqueous medium and the cell membrane of the living cell, and further including the steps of:
   a) disposing the vesicle and a living cell into an aqueous medium; and
   b) exposing the vesicle, the living cell and the aqueous medium to a solute which, at a sufficient partial pressure of the solute, substantially dissolves in the aqueous solvent medium, whereby a portion of the dissolved solute migrates to a hydrophobic fatty acyl portion of the lipid bilayer of both the vesicle and the living cell, and which allows migration of the molecule from the vesicle and across the cell membrane of the living cell; and
   c) exposing the aqueous solvent medium, the vesicle and the living cell to a sufficient partial pressure of the solute to cause the solute to substantially dissolve in the aqueous medium, whereby the solute migrates from the aqueous medium to the hydrophobic fatty acyl portion of the lipid bilayer of both the vesicle and the living cell, thereby allowing migration of the molecule from the vesicle and across the cell membrane of the living cell.

12. A method for delivering a molecule to a living cell, comprising the steps of:
   a) disposing a living cell and a vesicle in an aqueous solvent medium, the vesicle containing a molecule which is to be delivered to a lipid bilayer membrane of the living cell, in a lipid bilayer membrane of the vesicle;
   b) exposing the aqueous solvent medium, containing the living cell and the vesicle, to a solute which, at a sufficient partial pressure of the solute, dissolves in the aqueous solvent medium, a portion of the dissolved solute migrating to the hydrophobic fatty acyl portions of the lipid bilayers of both the living cell and the vesicle, thereby allowing migration of the molecule from the lipid bilayer membrane of the vesicle to the lipid bilayer of the living cell; and
   c) exposing the aqueous solvent medium, containing the living cell and the vesicle, to a sufficient partial pressure of the solute to cause the solute to dissolve in the aqueous solvent medium and to migrate to the hydrophobic fatty acyl portion of the lipid bilayers of both the living cell and the vesicle, whereby the molecule migrates from the lipid bilayer of the vesicle to the cell membrane of the living cell, thereby delivering the molecule to the cell membrane of the living cell.

13. A method for delivering a molecule to a living cell, comprising the steps of:
   a) disposing a living cell and a vesicle in an aqueous solvent medium, the vesicle containing a molecule which is to be delivered to the living cell;
   b) exposing the aqueous solvent medium, containing the living cell and the vesicle, to a solute which, at a sufficient partial pressure of the solute, dissolves in the aqueous solvent medium and migrates to the hydrophobic fatty acyl portions of the lipid bilayers of both the living cell and the vesicle, thereby causing migration of the molecule from the vesicle to the living cell; and
   c) exposing the aqueous solvent medium, containing the living cell and the vesicle, to a sufficient partial pressure of the solute to cause the solute to dissolve in the aqueous solvent medium and to migrate to the hydrophobic fatty acyl portion of the lipid bilayers of both the living cell and the vesicle, whereby the molecule migrates from the vesicle to the living cell, thereby delivering the molecule to the living cell.

14. A method of claim 13 wherein the solute, during migration to the hydrophobic fatty acyl portion of the lipid bilayers of the living cell and vesicle, causes the cell membranes to fuse with each other, and wherein the fusion of cell membranes causes delivery of the molecules to the living cell.

15. The method of claim 14 wherein the solute includes a compound which is a hydrophobic gas at normal temperature and pressure.

16. The method of claim 15 wherein the solute includes methane.

17. The method of claim 15 wherein the partial pressure of the solute to which the aqueous solvent medium, containing the living cell and the vesicle, are exposed is in a range of between about 0.1 MPa and about 300 MPa.

18. The method of claim 17 wherein the temperature to which the aqueous solvent medium, containing the living cell and the vesicle, and the solute are exposed is in a range of between about 0° C. and about 60° C.

19. A system for causing increased migration of a molecule across a lipid bilayer membrane, comprising:
   a) a high-pressure vessel;
   b) a container disposed within the high-pressure vessel for containing an aqueous solvent having a lipid bilayer and a molecule disposed therein;
   c) means for pressurizing the reaction vessel with a solute which, at sufficient partial pressure of the solute, dissolves in the aqueous solvent and migrates to a hydrophobic fatty acyl portion of the lipid bilayer membrane, the amount of solute in the hydrophobic fatty acyl portion of the lipid bilayer membrane being sufficient to cause increased migration of the molecule across the lipid bilayer membrane, the means for pressurizing enabling a sufficient partial pressure of the solute to cause a sufficient amount of the solute to migrate to the hydrophobic fatty acyl portion of the lipid bilayer membrane to cause increased migration of the molecule across the lipid bilayer membrane.

20. A system for causing increased migration of a molecule across a lipid bilayer membrane, comprising:
   a) means for combining an aqueous solvent medium, in which the lipid bilayer membrane and a molecule, which can migrate across the lipid bilayer membrane, are disposed, with a solute which, at a sufficient partial pressure of the solute, dissolves in the aqueous solvent medium, a portion of the dissolved solute migrating to a hydrophobic fatty acyl portion of the lipid bilayer membrane, and which causes increased migration of the molecule across the lipid bilayer membrane when a portion of the solute is dissolved in the aqueous solvent medium and when a portion of the solute is disposed in the hydrophobic fatty acyl portion of the lipid bilayer membrane; and means for exposing the aqueous solvent medium and the lipid bilayer membrane to a sufficient partial pressure of the solute to cause the solute to dissolve in the aqueous solvent medium, whereby a portion of the solute migrates to the hydrophobic fatty acyl portion of the lipid bilayer membrane, thereby causing increased migration of the molecule across the lipid bilayer membrane.

21. A system for delivering a molecule to a living cell, comprising:
    a) means for disposing a living cell and a vesicle in an aqueous solvent medium, the vesicle containing a molecule which is to be delivered to a lipid bilayer membrane of the living cell, in a lipid bilayer membrane of the vesicle;
    b) means for exposing the aqueous solvent medium, containing the living cell and the vesicle, to a solute which, at a sufficient partial pressure of the solute, dissolves in the aqueous solvent medium, a portion of the dissolved solute migrating to the hydrophobic fatty acyl portions of the lipid bilayers of both the living cell and the vesicle, thereby causing migration of the molecule from the lipid bilayer membrane of the vesicle to the lipid bilayer of the living cell; and
    c) means for exposing the aqueous solvent medium, containing the living cell and the vesicle, to a sufficient partial pressure of the solute to cause the solute to dissolve in the aqueous solvent medium and to migrate to the hydrophobic fatty acyl portion of the lipid bilayers of both the living cell and the vesicle, whereby the molecule migrates from the lipid bilayer of the vesicle to the cell membrane of the living cell, thereby delivering the molecule to the cell membrane of the living cell.

22. A system for delivering a molecule to a living cell, comprising:
    a) means for disposing a living cell and a vesicle in an aqueous solvent medium, the vesicle containing a molecule which is to be delivered to the living cell;
    b) means for exposing the aqueous solvent medium, containing the living cell and the vesicle, to a solute which, at a sufficient partial pressure of the solute, dissolves in the aqueous solvent medium and migrates to the hydrophobic fatty acyl portions of the lipid bilayers of both the living cell and the vesicle, thereby causing migration of the molecule from the vesicle to the living cell; and
    c) means for exposing the aqueous solvent medium, containing the living cell and the vesicle, to a sufficient partial pressure of the solute to cause the solute to dissolve in the aqueous solvent medium and to migrate to the hydrophobic fatty acyl portion of the lipid bilayers of both the living cell and the vesicle, whereby the molecule migrates from the vesicle to the living cell, thereby delivering the molecule to the living cell.

23. A method for delivering a molecule to a living cell, comprising the steps of:
    a) disposing a living cell and a vesicle in an aqueous solvent medium, the vesicle containing a molecule which is to be delivered to the living cell;
    b) exposing the aqueous solvent medium, containing the living cell and the vesicle, to a solute which is a hydrophobic gas at about normal temperature and pressure, and which, at sufficient partial pressure of the solute, dissolves in the aqueous solvent medium and migrates to the hydrophobic fatty acyl portions of the lipid bilayers of both the living cell and the vesicle, thereby causing migration of the molecule from the vesicle to the living cell; and
    c) exposing the aqueous solvent medium, containing the living cell and the vesicle, to a sufficient partial pressure of the solute to cause the solute to dissolve in the aqueous solvent medium and to migrate to the hydrophobic fatty acyl portion of the lipid bilayers of both the living cell and the vesicle, whereby cell membranes of the living cell and the vesicle fuse with each other, thereby delivering the molecule to the living cell.

24. The method of claim 23 wherein the solute includes methane.

25. The method of claim 23 wherein the partial pressure of the solute to which the aqueous solvent medium, containing the living cell and the vesicle, are exposed is in a range of between about 0.1 MPa and about 300 MPa.

26. The method of claim 25 wherein the temperature to which the aqueous solvent medium, containing the living cell and the vesicle, and the solute are exposed is in a range of between about 0° C. and about 60° C.

* * * * *

UNITED STATES PATENT AND TRADEMARK OFFICE
CERTIFICATE OF CORRECTION

PATENT NO. : 5,284,588
DATED : February 8, 1994
INVENTOR(S) : Lee C. Makowski, Hoshang F. Batliwala, Thayumanasamy Somasundaram and Egidijus E. Uzgiris It is certified that error appears in the above-identified patent and that said Letters Patent is hereby corrected as shown below:

On title page, item [75]

Inventors: change
After "Batiwala, Boston" delete --both of Mass.--
and insert --Thayumanasamy Somasundaram, Boston, all of Mass.; and Egidigus E. Uzgiris, Schenectady, N.Y.--;

Claim 1, column 14, line 55:
After the word "and" insert --b)--;

Claim 6, column 15, line 4:
After the word "nucleic" insert --acid--;

Claim 20, column 17, line 12:
After the word "and" insert --b)--.

Signed and Sealed this

Fifth Day of July, 1994

BRUCE LEHMAN

*Attest:*

*Attesting Officer*  *Commissioner of Patents and Trademarks*